(12) United States Patent
Papangelou et al.

(10) Patent No.: US 10,064,983 B2
(45) Date of Patent: Sep. 4, 2018

(54) MODIFIED POROUS MATERIALS AND METHODS OF CREATING INTERCONNECTED POROSITY IN MATERIALS

(71) Applicant: Arthrex, Inc., Naples, FL (US)

(72) Inventors: Christopher G. Papangelou, Bonita Springs, FL (US); G. Joshua Karnes, Naples, FL (US)

(73) Assignee: Arthrex, Inc., Naples, FL (US)

( * ) Notice: Subject to any disclaimer, the term of this patent is extended or adjusted under 35 U.S.C. 154(b) by 71 days.

(21) Appl. No.: 15/133,600

(22) Filed: Apr. 20, 2016

(65) Prior Publication Data
US 2016/0228619 A1 Aug. 11, 2016

Related U.S. Application Data

(63) Continuation of application No. 14/152,507, filed on Jan. 10, 2014, now Pat. No. 9,345,817.

(60) Provisional application No. 61/770,703, filed on Feb. 28, 2013.

(51) Int. Cl.
| *A61L 31/04* | (2006.01) |
| *A61L 31/14* | (2006.01) |
| *A61L 31/06* | (2006.01) |
| *A61L 31/02* | (2006.01) |

(52) U.S. Cl.
CPC .......... *A61L 31/146* (2013.01); *A61L 31/028* (2013.01); *A61L 31/048* (2013.01); *A61L 31/06* (2013.01); *A61L 31/148* (2013.01)

(58) Field of Classification Search
CPC ...... A61L 31/028; A61L 31/048; A61L 31/06; A61L 31/146; A61L 31/148
See application file for complete search history.

(56) References Cited

U.S. PATENT DOCUMENTS

| 4,892,544 | A | 1/1990 | Frisch |
| 5,856,367 | A | 1/1999 | Barrows et al. |
| 6,235,225 | B1 | 5/2001 | Okada et al. |
| 6,436,426 | B1 | 8/2002 | Liao et al. |
| 7,943,677 | B2 | 5/2011 | Papangelou et al. |
| 2005/0246021 | A1 | 11/2005 | Ringeisen |
| 2006/0197063 | A1 | 9/2006 | Tennison et al. |
| 2008/0234730 | A1* | 9/2008 | Cotton .......... 606/232 |
| 2009/0208586 | A1 | 8/2009 | Sajiki |
| 2009/0222091 | A1 | 9/2009 | Morrissette et al. |
| 2009/0246873 | A1 | 10/2009 | Yamamoto et al. |
| 2010/0221303 | A1 | 9/2010 | Le Visage |
| 2011/0276133 | A1 | 11/2011 | Liu |

* cited by examiner

*Primary Examiner* — Irina S Zemel
(74) *Attorney, Agent, or Firm* — McDonnell Boehnen Hulbert & Berghoff LLP

(57) ABSTRACT

Techniques, mixtures and improved porous materials (interconnected porous constructs) that are capable of maintaining a sufficient porosity while conferring improved mechanical and physical strength to the final construct. A sacrificial construct (for example, a sacrificial material such as polymethyl methacrylate (PMMA)) is used to obtain an inverse porosity of the construct it was molded into. The process provides a less porous end material that may be used as an arthroplasty device or surgical implant (for example, an interference screw of suture anchor) among many other applications. The process employs a sacrificial material to reduce the porosity of the final construct to about 35%.

8 Claims, 3 Drawing Sheets

MODIFIED POROUS MATERIALS AND METHODS OF CREATING INTERCONNECTED POROSITY IN MATERIALS

CROSS-REFERENCE TO RELATED APPLICATIONS

This is a continuation of U.S. application Ser. No. 14/152,507, filed Jan. 10, 2014, which claims the benefit of U.S. Provisional Application No. 61/770,703, filed Feb. 28, 2013, the disclosures of which are incorporated by reference in their entireties herein.

FIELD OF THE INVENTION

The present invention relates to the field of surgery and, more particularly, to modified porous materials and improved technologies for creating and controlling porosity in materials.

BACKGROUND OF THE INVENTION

Porous materials are widely used in biomedical and industrial applications. In the biomedical field, porous materials have been used as scaffolds (templates) for tissue engineering/regeneration, wound dressings, drug release matrices, membranes for separations and filtration, absorbents and hemostatic devices, among many others.

Despite their extensive use, the development of porous materials has been affected due to the difficulty of making an article porous and keeping it so while providing the material (article) with adequate strength. For example, porous polymer materials have been used as scaffolds for cell incorporation, proliferation and tissue regeneration in aqueous environments (such as in a tissue culture medium, or implanted inside a human or animal body). Yet, such porous polymers must also possess sufficient mechanical strength to withstand anatomical pressures and deformations, and also be capable of maintaining their structure and function when undergoing various changes (for example, mechanical or environmental changes).

A need exists for techniques for creating and controlling porosity in materials to obtain a less porous material than the one obtained by traditional methods. Also needed are methods of forming a porous material with a modified, interconnected porosity that renders the material sufficiently strong and substantially stable in a predetermined environment. Also needed is an implant that is at least partially porous to provide a scaffold for bone cells to grow into, but is also strong enough to withstand fabrication processes such as machining and/or molding, among many others.

BRIEF SUMMARY OF THE INVENTION

The present invention provides techniques, mixtures and improved porous materials (interconnected porous constructs) that are capable of maintaining a sufficient porosity while conferring improved mechanical and physical strength to the final construct.

The present invention uses a sacrificial construct (for example, a sacrificial material such as polymethyl methacrylate (PMMA)) to obtain an inverse porosity of the construct it was molded into. The process provides a less porous end material that may be used as an implant (for example, an arthroplasty device, screw or anchor) among many other applications. The process employs a sacrificial material to reduce the porosity of the final construct to about 35%.

Other features and advantages of the present invention will become apparent from the following description of the invention.

DETAILED DESCRIPTION OF THE INVENTION

Figure 1:
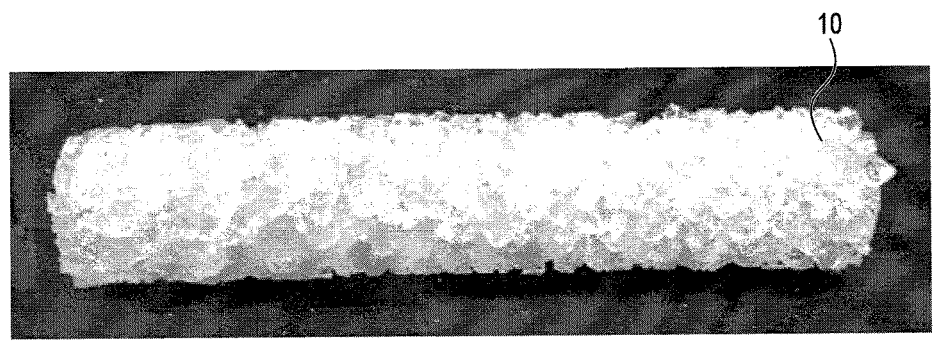
FIG. 1 illustrates an image of merged PVA particles to form an interconnected construct according to an exemplary embodiment of the present invention.
Figure 2:
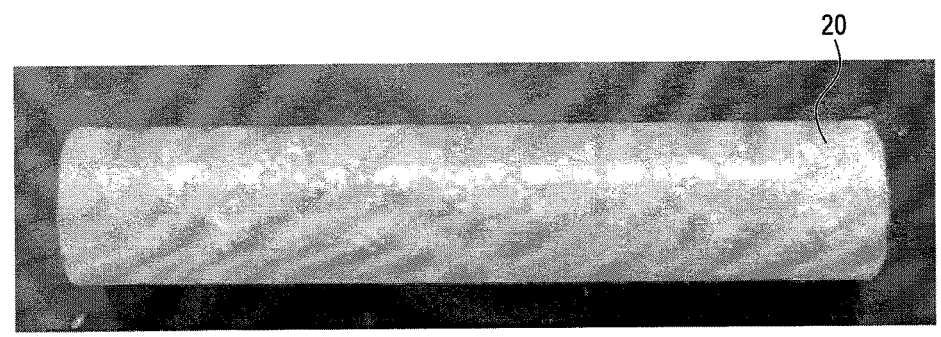
FIG. 2 illustrates an image of PMMA molded into the interconnected porous PVA construct of FIG. 1.
Figure 3:
FIG. 3 illustrates an image of porous PMMA sample after dissolving PVA.
Figure 4:
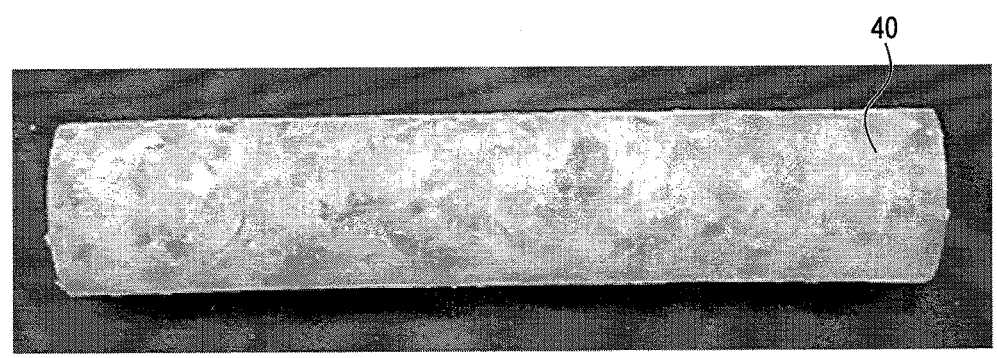
FIG. 4 illustrates an image of a casting material molded into the porous PMMA sample of FIG. 3.

The present invention provides techniques and mixtures for creating and controlling porosity in materials to obtain a less porous material than the one obtained by traditional methods. The final porous material has a modified, interconnected porosity that renders the material substantially stable in a predetermined environment.

The present invention uses a sacrificial construct (for example, a sacrificial material such as polymethyl methacrylate (PMMA)) to obtain an inverse porosity of the construct it was molded into (to reduce the porosity from about 65% to about 35%). The process provides a less porous end material that may be used as a surgical implant, an arthroplasty device, an interference screw, an anchor such as a suture anchor, an implant (for example, a femoral implant such as a PLLA screw), among many other applications.

The present invention provides a method of creating a porous material by inter alia the steps of: (a) creating a porous structure from a soluble material; (b) filling the void area of the soluble porous structure with a non-soluble material; (c) curing the soluble and non-soluble material; (d) removing the soluble material to obtain a newly-formed porous material; (e) filling the void area of the newly-formed soluble porous structure with a non-soluble material; and (f) removing the soluble material to obtain a porous material.

The present invention also provides a method of creating a porous material by inter alia the steps of: (a) creating an interconnected porous structure from a water soluble material (the water soluble material may be a hydrogel such as polyvinyl alcohol); (b) filling the void area of the water soluble interconnected porous structure with a non-soluble material (the non-soluble material may be an acrylic such as polymethyl methacrylate (PMMA)); (c) curing the soluble and non-soluble material; (d) removing the water soluble material to obtain a newly-formed interconnected porous material; (e) filling the void area of the newly-formed soluble interconnected porous structure with a non-soluble material (the non-soluble material may be a bioresorbable material); and (f) removing the soluble material to obtain an interconnected porous material (the soluble material can be removed by an organic solvent, the organic solvent can belong to an alcohol group such as isopropyl or ethanol; the organic solvent can belong to an ether group; the organic solvent can belong to an vinyl group).

An exemplary method of forming an improved interconnected porous construct according to an embodiment of the present invention is detailed below with reference to FIGS. 1-5. The process detailed below with reference to FIGS. 1-5 may be conducted with steps similar to the method of producing a porous construct as detailed in U.S. Pat. No. 7,943,677, issued May 17, 2011, the disclosure of which is incorporated in its entirety by reference herein. As detailed in U.S. Pat. No. 7,943,677, a solvent merging/particulate-leaching method is used to produce interconnected volumetric porosity.

An illustrative embodiment of the invention includes a method of producing a porous construct by creating negative porosity twice in the same process. In a first step, a plurality of soluble particles are merged in the presence of a solvent, e.g., an inorganic acid such a phosphoric acid or a compound. In one embodiment, the compound comprises about 5% phosphoric acid and 95% distilled water. In a preferred embodiment, the plurality of soluble particles are water soluble, such as PVA.

The soluble particles are then dried for about 24 hours and a first casting material (such as PMMA) is added to fill the void area of the water soluble PVA material. Curing of the first casting material and the plurality of soluble polymer particles for about 48 hours results in a polymerized construct.

Once cured, the construct is exposed so that the water soluble particles are dissolved away. In one embodiment, the soluble particles are dissolved in warm water between about 85° Celsius and the $T_g°$ of the cross-linking polymer. Preferably the soluble particles are dissolved in a solvent, such as water, at a temperature below the $T_g°$ of the first casting material. Removal of the water soluble particles produces a newly-formed interconnect porous structure of the first non-soluble casting material (PMMA), i.e., by dissolving the merged soluble particles, interconnected pores are produced throughout at least a volumetric portion of the first non-soluble casting material forming a porous construct.

The above steps set forth in the previous three paragraphs are repeated for filling the void area of the interconnect porous structure of the first non-soluble casting material (PMMA) with a second non-soluble casting material, which is then subjected to removal of the first non-soluble casting material (PMMA) to obtain a final interconnected porous material formed of the second non-soluble casting material with a porosity of about 35%.

The second casting material may be any material that is cast and below the melting temperature of the other material. For example, the casting material may be any degradable or biodegradable polymer (or combination of such polymers) such as PLLA (poly-L-lactide acid or poly-L-lactic acid), PLA (poly lactic acid), PLGA (co-poly lactic acid/glycolic acid), simple linear polymers such as PGL (polyglycerol), PGA (polyglycolic acid) or caprolactone-based polymers such as PCL, among many other monomers, polymers, block copolymers, linear polyesters, etc. In an exemplary-only embodiment, and as detailed below, PLLA is employed as an exemplary material to explain the process of the present invention.

PVA is preferred to create porosity in the materials for its fast dissolving rate. The process employs a mild phosphoric acid.

Figure 5:
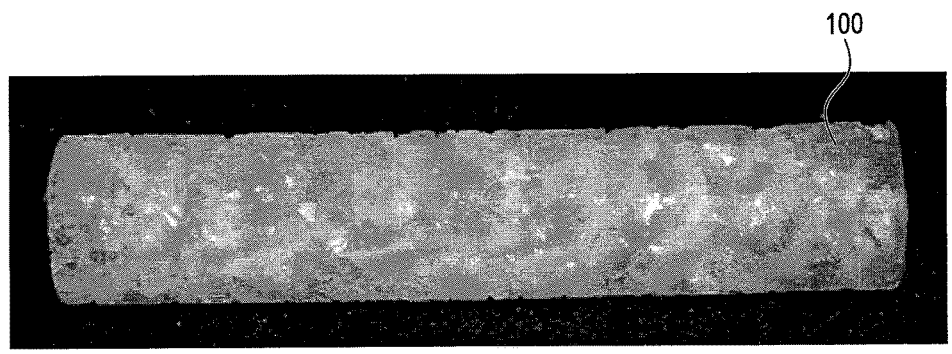
FIG. 5 illustrates an image of a casting material porous sample after dissolving PMMA using alcohol.

An exemplary method of the present invention is set forth below with reference to FIGS. 1-5 and by the following steps:

1) Creating an interconnected porous structure 10 (FIG. 1) by merging a plurality of water soluble particles (PVA) using a mild phosphoric acid;
2) Drying the plurality of water soluble PVA particles;
3) Filling the void area of the water soluble interconnected porous structure with PMMA to form construct 20 (FIG. 2);
4) Removing the water soluble material to obtain a newly-formed interconnected porous PMMA material 30 (FIG. 3);
5) Filling the void area of the newly-formed soluble interconnected porous structure with casting material (for example, PLLA) to form construct 40 (FIG. 4); and
6) Removing the soluble material using isopropyl alcohol to obtain an interconnected porous material 100 (FIG. 5).

According to another exemplary-only embodiment, a method of creating interconnected porosity in materials comprises the steps of: (i) merging a plurality of soluble particles; (ii) applying a non-soluble casting material to the merged soluble particles; (iii) curing the non-soluble casting material and merged soluble particles; (iv) dissolving the merged soluble particles; (v) applying another non-soluble casting material to the porous construct; (vi) curing the non-soluble casting material and porous construct; and (vii) dissolving the porous construct.

According to yet another exemplary-only embodiment, a method of forming an interconnected porous material comprises the steps of: (i) providing a porous structure of a first material having a first solubility; (ii) applying a second material to the porous structure, the second material having a second solubility which is different from the first solubility; (iii) curing the first and second materials; (iv) removing the first material to obtain a newly-formed porous structure, the first material being removed with a first biocompatible solvent that affects the first material but not the second material; (v) applying a third material to the newly-formed porous structure, the third material having a solubility different from that of the first and second materials; (vi) curing the third material and the newly-formed porous structure; and (vii) removing the second material to obtain the final interconnected porous construct, the second material being removed with a second biocompatible solvent that affects the second material but not the third material.

The methods of the present invention have particular applicability to the formation and fabrication of a variety of constructs and implants, for example, arthroplasty devices and implants, interference screws (such as exemplary PLLA screws), suture anchors, i.e., any variety of constructs that are at least partially porous (about 35% porosity) to provide a scaffold for bone cells to grow into, but are also strong enough to withstand fabrication processes such as machining and/or molding, among many others (to form the final implant/construct).

The present invention provides methods and porous structures that are formed by creating negative porosity twice during the process and by carefully selecting the materials and solvents corresponding to each step. For example, and as detailed above, the second material must be selected so that it can allow for it to be selectively removed without affecting the casting material, i.e., the third material; the second material must be also biocompatible. Similarly, the solvent of the first material must be selected so that it cannot affect the solubility and removal rate of the other materials and must be also biocompatible. Thus, to allow the solvent merging/particulate-leaching process to be conducted twice, all materials must be carefully selected based on the solubility/removal rate relative to each other.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A construct comprising an interconnected porous structure with inverse porosity comprising a sacrificial material, wherein the sacrificial material is polymethyl methacrylate, and a degradable polymer.

2. The construct of claim 1, wherein the construct is an implant.

3. The construct of claim 1, wherein the construct is a screw.

4. The construct of claim 3, wherein the screw is an interference screw.

5. The construct of claim 1, wherein the construct is a suture anchor.

6. The construct of claim 1, wherein the degradable polymer has a porosity of about 35%.

7. The construct of claim 1, wherein the degradable polymer is biodegradable.

8. The construct of claim 1, wherein the degradable polymer is selected from the group consisting of poly-L-lactic acid (PLLA), polylactic acid (PLA), co-polylactic acid/glycolic acid (PLGA), polyglycerol (PGL), polyglycolic acid (PGA), polycaprolactone (PCL), and combinations thereof.

* * * * *